United States Patent [19]

Weinstein et al.

[11] Patent Number: 5,388,634
[45] Date of Patent: Feb. 14, 1995

[54] CARDIOPLEGIA DELIVERY SYSTEM

[75] Inventors: Martin J. Weinstein, Salisbury; Kenneth E. Buckler, Dracut, both of Mass.

[73] Assignee: C. R. Bard, Inc., Murray Hill, N.J.

[21] Appl. No.: 58,245

[22] Filed: May 10, 1993

[51] Int. Cl.⁶ .............................................. F28F 7/00
[52] U.S. Cl. .................................. 165/78; 165/67; 604/122; 251/149.6
[58] Field of Search ............... 165/67, 76, 78, 156; 604/122; 251/149.6

[56] References Cited

U.S. PATENT DOCUMENTS

| | | |
|---|---|---|
| 1,622,006 | 3/1927 | Seligman ........................ 165/78 |
| 2,092,116 | 9/1937 | Hansen ........................ 251/149.6 |
| 4,065,264 | 12/1977 | Lewin . | 
| 4,540,399 | 9/1985 | Litzie et al. ........................ 604/122 |
| 4,559,999 | 12/1985 | Sérvas et al. . | 
| 4,653,577 | 3/1987 | Noda . | 
| 4,846,177 | 7/1989 | Leonard . | 
| 4,883,455 | 11/1989 | Leonard . |

FOREIGN PATENT DOCUMENTS

| | | | |
|---|---|---|---|
| 2651015 | 5/1978 | Germany ........................ 165/78 |
| 3003398 | 8/1980 | Germany ........................ 165/78 |
| 3241584 | 5/1984 | Germany ........................ 165/67 |

*Primary Examiner*—A. Michael Chambers
*Attorney, Agent, or Firm*—Dennison, Meserole, Pollack & Scheiner

[57] ABSTRACT

A holder for a heat exchanger in a cardioplegia delivery system including dual couplers releasably engageable with the inlet and outlet ends of the heat exchanger. A one-way shut-off valve is associated with each coupler and opened to provide communication upon mounting of the heat exchanger. The valves automatically close upon release of the heat exchanger. A release member engages both couplers and is manually retractable to simultaneously open both couplers for release of both heat exchanger fittings for instantaneous release of the heat exchanger and a closing of the associated valves.

11 Claims, 3 Drawing Sheets

CARDIOPLEGIA DELIVERY SYSTEM

Cardioplegia delivery systems, intended to warm or cool blood/crystalloid solutions administered to a patient during surgical procedures such as open-heart surgery, basically comprise a heat exchanger, inlet and outlet fittings for the heat-exchanging fluid, and inlet and outlet fittings for the blood/solution to be treated.

The heat exchanger component, because of the direct flow of blood therethrough, and the potential for contamination, is normally a disposable item typically connected to the heat-exchanging fluid lines, normally a cold water inlet and a cold water outlet, by quick-disconnect couplers. One such commonly used coupler is known as a "Hansen" coupler and basically comprises, within a socket adapted to receive an inlet or outlet fitting, a plurality of peripherally spaced, inwardly biased detents selectively retracted by an axially movable sleeve. Insertion of the inlet/outlet fitting effects a radial outward retraction of the detents for subsequent engagement thereof within an annular groove about the inlet/outlet fitting which precludes disengagement.

Upon a seating of the inlet/outlet fitting within the coupler, liquid flow can be accommodated therethrough. Release of the fitting from the coupler is effected by an axial shifting of the sleeve to forcibly outwardly retract the detents.

The couplers for the heat-exchanging fluid are normally individually engaged directly between each of the fluid lines and the respective inlet and outlet fittings on the heat exchanger.

The engaged couplers and fittings are not normally capable of supporting the heat exchanger during use, and provision must be made for separately clamping the heat exchanger to an appropriate support stand.

A preferred form of heat exchanger is of a generally horseshoe or U-shaped configuration with the water inlet and outlet fittings at the free ends of the two legs. A heat exchanger of this general type will be noted in U.S. Pat. No. 4,653,577 to Noda. The heat exchanger in this patent, as is typical, directly connects to the water supply and water outlet lines, which must be separately engaged and disengaged.

SUMMARY OF THE INVENTION

The present invention is concerned with the mounting and release of a disposable heat exchanger to and from the lines supplying the water or other heat-exchange fluid.

It is a significant object of the invention to utilize a quick connect/disconnect system whereby the water supply lines can be simultaneously and instantaneously communicated with and disengaged from both the water inlet fitting and the outlet fitting of the disposable heat exchanger.

It is an additional object of the invention to provide for a coupling system wherein the heat exchanger is fully supported in operative position upon engagement with the quick connect coupling means, and without requiring an additional support structure.

It is also contemplated that one-way shut-off valves be cooperatively associated with the releasable couplers for the fittings to provide for water flow only when the heat exchanger is mounted and to automatically discontinue flow upon release and removal of the heat exchanger.

The disposable heat exchanger itself is of the type wherein the inlet and outlet fittings are generally parallel to each other and provided on the free ends of a pair of heat exchanger legs. The legs are joined by a bight portion to provide for continuous flow from one fitting to the other.

The invention comprises a holder which is adapted to clamp mount to a support stand and provide both a mount for the heat exchanger and communication between the hospital water lines and the heat exchanger.

The holder includes fittings which, through appropriate connectors, receive the inlet/outlet water lines. The holder fittings communicate, through internal passages within the holder, to projecting valved quick connect couplers which in turn receive the fitting ends of the heat exchanger therein and in a manner which controls the internal valves to allow flow through the heat exchanger upon mounting and to discontinue flow upon removal.

Coupling of the heat exchanger fittings with the associated couplers is achieved by a simultaneous inward engagement of both heat exchanger fittings within the couplers. In order to facilitate this simultaneous engagement, and more importantly to provide for simultaneous disengagement, a release member joins and extends between the couplers whereby the user, with a single hand, can simultaneously release both couplers and allow for withdrawal of the heat exchanger. Withdrawal of the heat exchanger, and simultaneously disengaging both heat exchanger fittings, results in an immediate closing of the shut-off valves and a cessation of flow of the heat exchanging fluid.

The holder, upon release of the disposable heat exchanger, is immediately ready for the mounting of another heat exchanger.

In order to facilitate manipulation of the single release bar or member, the holder is configured to form a hand grip in the manner of a cross bar which parallels the central or gripping portion of the release member. In this manner, the user's hand can encircle the grip or cross bar with the cross bar nesting in the palm of the hand and providing a resistance against which the release member can be inwardly drawn by the fingers.

Other features of the invention will become apparent from the more detailed description of the invention following hereinafter.

DESCRIPTION OF PREFERRED EMBODIMENT

Figure 1:
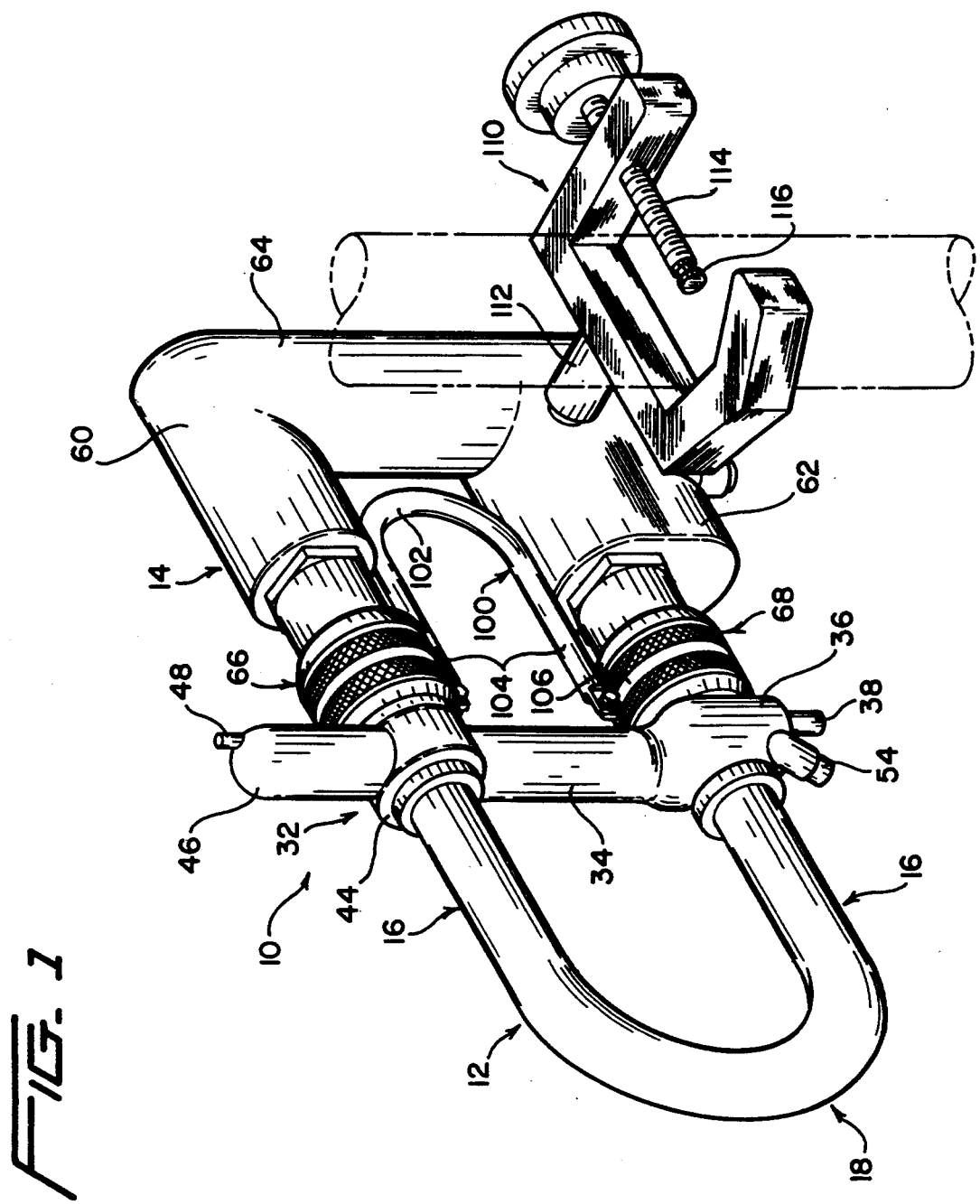
FIG. 1 is a perspective view of the cardioplegia delivery system with the heat exchanger mounted to the holder.

Referring now more specifically to the drawings, the cardioplegia delivery system 10 of the invention basically comprises a heat exchanger 12 and a holder 14.

The heat exchanger 12, preferably of a generally horseshoe or U-shaped configuration, includes opposed legs 16 interconnected at one end by a bight portion 18 and terminating at the opposite ends in male quick connect inlet and outlet fittings 20 and 22.

The fittings 20 and 22 are preferably integrally defined on the opposed end portions of a stainless steel heat exchange element 24 having spiral flutes defined about the exterior thereof and for a major portion of the length thereof commencing inwardly of the end fittings 20 and 22. The heat exchange element forms a continuous internal flow passage between the inlet and outlet end fittings for passage of the heat exchanging fluid or water therethrough.

The fluted central portion of the heat exchange element 24 is encased within a PVC tube 28 in intimate contact with the outer spiraling edges of the flutes to force the blood or solution to spiral through the tube 28 as it moves through the heat exchanger 12.

A housing 32 of high impact inert resin, such as a polycarbonate, extends transversely between the heat exchanger legs 16 inwardly of the inlet and outlet end fittings 20 and 22, and in direct communication with the opposed ends of the tube 28 encasing the heat exchange element 24.

Figure 2:
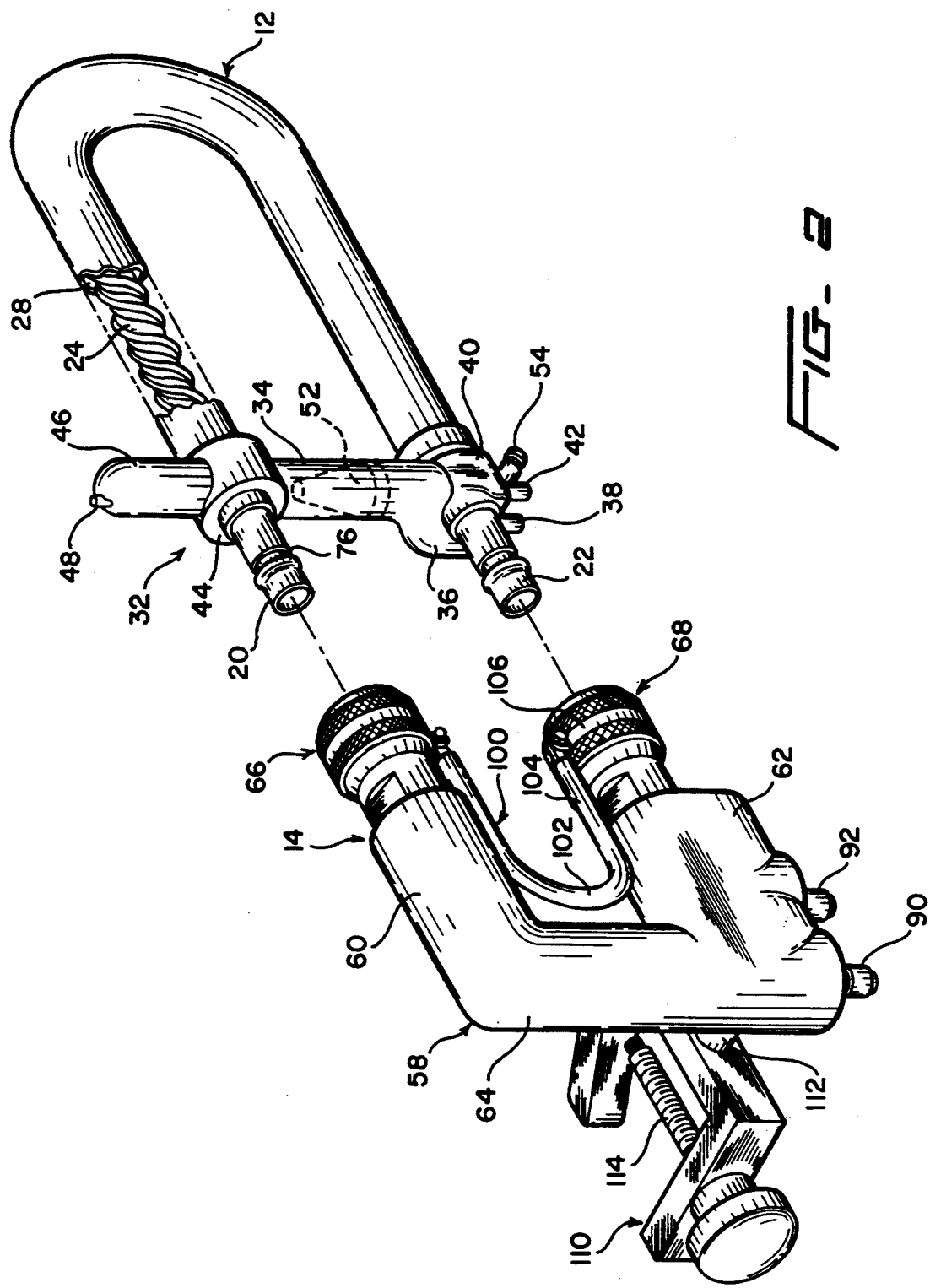
FIG. 2 is a reverse perspective view of the system with the heat exchanger released from the holder.
Figure 3:
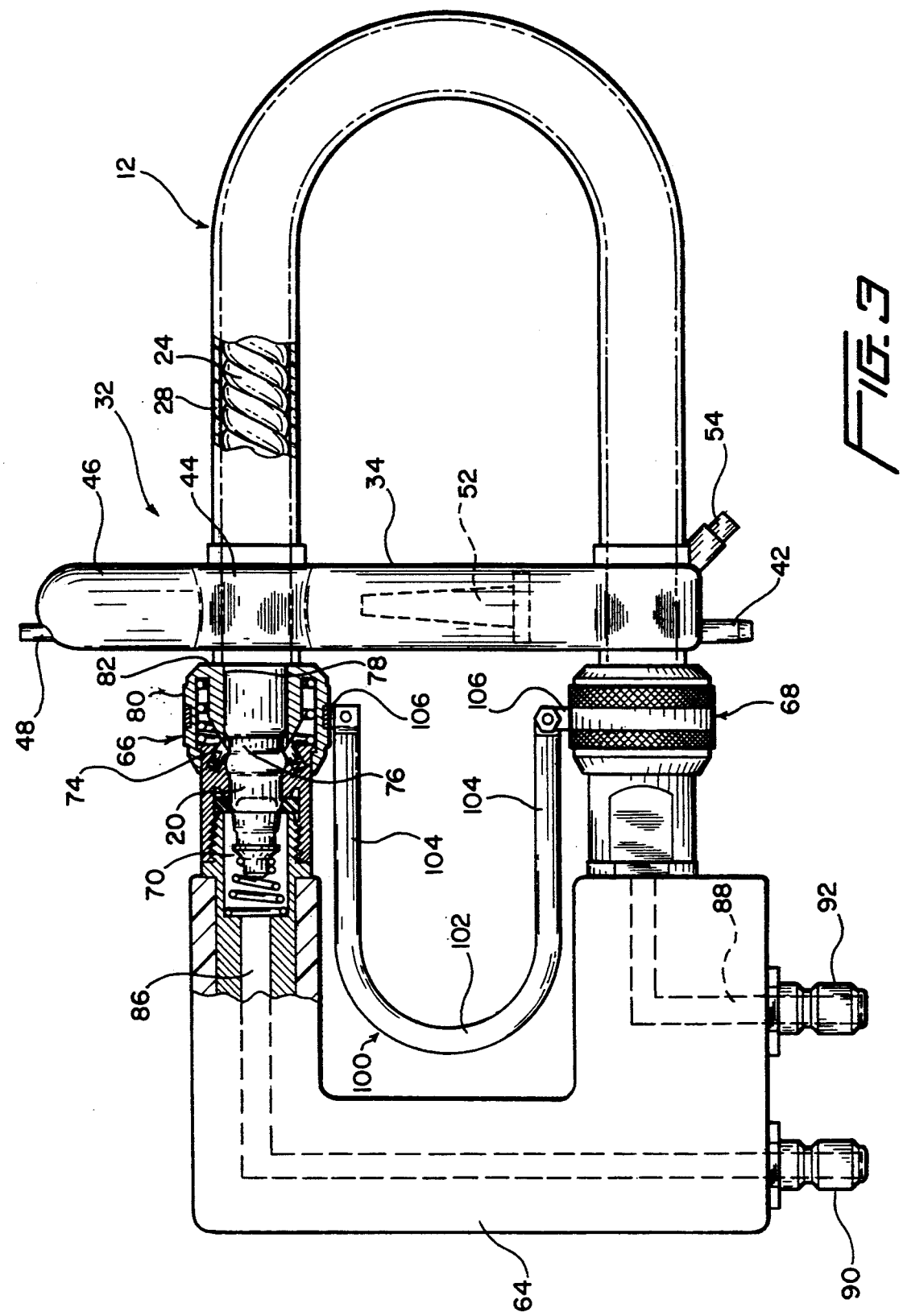
FIG. 3 is an enlarged elevational view of the holder with a portion in cross section for purposes of illustration.

With the heat exchanger 12 in its normal operating position extending horizontally and vertically oriented as in FIGS. 1 and 2, the housing 32 includes an upright cross tube 34 with an integral laterally offset depending bypass 36 at the lower end thereof, the bypass 36 having an integral outwardly extending outlet fitting 38. A separate intake chamber 40, fixed to but out of communication with the cross tube 34 and bypass 36, nests against the bypass 36 and including a downwardly directed integral inlet fitting 42. This intake chamber 40 directly communicates with the adjacent end of the spiral flow passage or passages within the tube 28.

The upper end of the cross tube 34 of the housing 32 communicates directly with an annular chamber 44 encircling the upper heat exchanger leg 16 and in turn in flow permitting communication with the corresponding end of the tube 28.

The housing 32, above the annular chamber 44 includes an upwardly extending air chamber 46 with an upwardly directed luer port 48.

The cross tube portion 34 of the housing 32 includes a blood filter/screen 52, and in combination with the bypass lower portion 36 thereof defines a blood chamber with which an appropriate temperature probe 54 communicates.

In use, the blood and/or solution lines are engaged with the inlet and outlet fittings 42 and 38. The fluid to be treated, utilizing appropriate pump means, flows inwardly through the inlet fitting 42 into the intake chamber 40, and from there through the PVC tubing 28 and the spiraling passages defined therein about the exterior of the heat exchange element 24. The treated fluid exits the tubing 28 into the annular chamber 44, at which point any air entrained in the flow will rise within the air chamber 46. The fluid itself flows downwardly through the cross tube 34 and through the filter/screen 52, past the temperature probe 54 and out the outlet fitting 38.

The actual heating or cooling of the treated fluid occurs within the tube 28 as the fluid spirals therealong and as a result of water or other heat exchanging fluid flowing internally through the heat exchange element 24 from the inlet end fitting 20 to the outlet end fitting 22 as shall be described subsequently.

The holder 14 comprises a body 58 of high impact inert resin, such as a polycarbonate, with upper and lower generally parallel arms 60 and 62 interconnected at one end by integral cross bar 64. The free outer ends of the arms 60 and 62 mount quick connect/disconnect connectors or couplers 66 and 68 respectively. The couplers 66, 68 are duplicate female couplers of a known construction adapted to receive and releasably retain the heat exchanger end fittings 20 and 22.

Each of the couplers basically includes an internal spring loaded valve 70 which is unseated or opened in response to full insertion of the corresponding end fitting 20 or 22. In addition, and in order to effect the actual releasable coupling, the coupler includes, annularly about an inner receiving surface or socket, a series of detents 74 which are urged radially inward to engage annularly about a retaining groove 76 defined circumferentially about the corresponding heat exchanger end fitting 20 or 22.

In order to outwardly retract the detents 74, an internal sleeve 76 is received within each socket and spring biased axially outward to allow radial inward extension of the detents 74 for engagement with an introduced end fitting 20 or 22. The detents are so configured and biased as to radially retract upon axial introduction of the appropriate end fitting with the detents subsequently radially inwardly extending into the fitting retaining groove 76. The detent retracting sleeve 78 is joined to an outer surrounding collar 80 by an outer end flange or cap 82. An internal spring 84 or like means engaged against the end cap 82 between the sleeve 78 and collar 80 biases the sleeve longitudinally outward to allow radial inward extension of the detents to the locked position. In order to release the detents 74 both to facilitate engagement of the fitting if desired, and more particularly to effect a quick disconnect of the fitting from the coupler, one need merely grasp the appropriate manipulating collar 80 and shift the collar and internal sleeve 78 axially inward to retract the detents 74 from the fitting groove 76. The fitting is then easily slid from the coupler 66,68.

The couplers 66 and 68 communicate, through internal passages 86 and 88 within the holder, with inlet and outlet fittings 90 and 92 respectively for the heat exchange fluid or medium, for example water. These fittings 90 and 92, as desired, may be of the type adapted for quick connect utilizing standard couplers. The internal flow passages 86 and 88 may be defined directly within the resin body of the holder or as tubular extensions of the fittings 90 and 92 and the associated couplers 66 and 68.

As previously noted, it is a particularly significant object of the invention to provide for the simultaneous quick connect/disconnect of the heat exchanger 12. As such, and as will be recognized from the drawings, the couplers 66 and 68 on the holder 14 are positioned to align with and directly receive the heat exchanger end fittings 20 and 22 upon a single inward movement of the heat exchanger toward the holder. Until such time as the heat exchanger fittings 20 and 22 are fully seated within the couplers 66 and 68, flow of the heat exchanging medium is prevented by the internal one-way valves. Upon fully seating the heat exchanger, the valves are open and flow through the heat exchanger is effected.

In order to effect simultaneous and substantial instantaneous release of the heat exchanger 12 from the holder 14, which will at the same time effect a closing of the one-way valves, a release bar or member 100 is fixed to and extends between the opposed collar and sleeve assemblies of the couplers 66 and 68. In its preferred form, the release bar or member 100 is of a generally U-shape with a central or intermediate bight 102 spaced forwardly from the cross bar 64 of the housing body and with the two legs 104 of the release member generally paralleling the upper and lower arms. The free ends of the arms 104 are secured to the collars 80 preferably by bolting between the ends of split ring clamps 106 which engage about the respective coupler collars 80. So configured, it will be appreciated that the release member 100 nests within the generally U-shaped body 58 of the holder 14. With the release member 100, simultaneous release of the two couplers 66 and 68 is easily effected by positioning the palm of a hand against the body cross bar 64, curling the fingers of the hand about and grasping the bight portion 102 of the release member 100, and squeezing to effect a relative rearward retraction of the release member 100 and a corresponding retraction of the coupler collars 80 and detent-releasing internal sleeves 78. Simultaneously with this action, the other hand of the user can grasp and outwardly withdraw the heat exchanger 12. Withdrawal of the heat exchanger, as previously indicated, will effect an automatic and instantaneous closing of the one-way valves internally of the couplers 66 and 68. The actual configuration of the release bar or member 100 can vary from that illustrated. However, it is essential that this member extend between and engage both couplers for simultaneous release. Further, it is particularly desirable that the release member 100 be so associated with the cross bar 64 of the body, or a corresponding portion thereof, whereby the body will provide a base against which the release member can be retracted, preferably utilizing a single hand whereby the second hand is available for engaging and withdrawing the released heat exchanger.

Upon a withdrawal of the heat exchanger, the heat exchanger itself, the only portion of the apparatus directly contacted by the blood or the like, can be disposed of. The holder component can be retained for reuse, and in fact can remain connected to the water lines with the internal one-way valves of the holder precluding flow therethrough until a new heat exchanger is mounted.

As previously indicated, the holder 14, in addition to providing for the quick connect and disconnect of the U-shaped heat exchanger 12, also functions as the sole means for mounting the heat exchanger. Thus, the holder has a C-type clamp 110 mounted thereto on a projecting stub 112 which may allow a degree of adjustable rotation of the clamp for proper positioning of the holder 14 in accord with the support structure to which the clamp is to lock. The support structure may be a portion of the pump console which is to control flow of the blood or cardioplegia solution, or an upright pole of a conventional support stand. As will be noted, the C-clamp basically utilizes a knob controlled threaded screw 114 engaged through one leg of the clamp and, through a bearing head 116 thereon, adapted to engage a support stand pole or the like against a second clamp leg, all in a relatively conventional manner.

The foregoing described embodiment is illustrative of the invention, and as other embodiments incorporating the inventive features of the invention may occur to those skilled in the art, the disclosed embodiment is not to be considered as a limitation on the scope of the invention.

We claim:

1. A holder for releasably mounting a heat exchanger in a cardioplegia delivery system, said heat exchanger defining a flow passage for a heat exchanging fluid and including an inlet fitting and an outlet fitting providing communication with said flow passage; said holder including inlet and outlet couplers positioned to align with and releasably engage with said inlet and outlet fittings respectively, said holder further including means for communicating said inlet and outlet couplers with a source and discharge for heat exchanging fluid, and release means engaged with and extending between said inlet and outlet couplers for manipulating and simultaneous release of said couplers, said couplers being quick disconnect couplers, each with retaining means adapted to engage and retain a fitting, and a movable component movably mounted for selectively releasing said retaining means, said release means being joined to said movable component of each of said couplers, said release means including a manually engageable portion for manipulation thereof and for simultaneous movement of said movable components, said holder including a gripping portion positioned in spaced opposition to said manually engageable portion on said release means and defining a fixed position base toward which said release means is relatively movable for simultaneous movement of said movable components and release of said retaining means of said inlet and outlet couplers.

2. The holder of claim 1 including first and second spaced arms having outer ends respectively mounting said inlet and outlet couplers, and inner portions interconnected by a cross member defining said gripping portion, said means for communicating said couplers with a source and discharge for heat exchanging fluid including a fluid inflow fitting for introduction of heat exchanging fluid, a fluid discharge fitting for discharge of heat exchanging fluid, and fluid inflow and outflow passages communicating said inflow and outflow fittings respectively with said inlet and outlet couplers.

3. The holder of claim 2 including valve means for precluding flow of heat exchanging fluid through said couplers in the absence of a mounted heat exchanger.

4. The holder of claim 3 wherein said release means comprises an elongate member having opposed ends fixed to said movable coupler components.

5. The holder of claim 4 wherein said elongate member includes a central portion extending generally along said cross member in laterally spaced relation thereto and defining said manually engageable portion, said elongate member including end portions extending from said central portion and along said arms outward to said couplers.

6. The holder of claim 5 including a clamp thereon having adjustable means for selective clamp-mounting of said holder to a support structure.

7. A holder for releasably mounting a heat exchanger in a cardioplegia delivery system, said heat exchanger defining a flow passage for a heat exchanging fluid and including an inlet fitting and an outlet fitting providing communication with said flow passage; said holder including inlet and outlet couplers positioned to align with and releasably engage with said inlet and outlet fittings respectively, said holder further including means for communicating said inlet and outlet couplers with a source and discharge for heat exchanging fluid, and release means engaged with and extending between said inlet and outlet couplers for manipulation and simultaneous release of said couplers, said couplers being quick disconnect couplers, each with retaining means adapted to engage and retain a fitting, and a movable component movably mounted for selectively releasing said retaining means, said release means being joined to said movable component of each of said couplers, said release means including a manually engageable portion for manipulation thereof and for simultaneous movement of said movable components, said holder including first and second spaced arms having outer ends respectively mounting said inlet and outlet couplers, and inner portions interconnected by a cross member, said means for communicating said couplers with a source and discharge for heat exchanging fluid including a fluid inflow fitting for introduction of heat exchanging fluid, a fluid discharge fitting for discharge of heat exchanging fluid, and fluid inflow and outflow passages communicating said inflow and outflow fittings respectively with said inlet and outlet couplers.

8. The holder of claim 7 wherein said release means comprises an elongate member having opposed ends fixed to said movable coupler components.

9. The holder of claim 8 wherein said elongate member includes a central portion extending generally along said cross member in laterally spaced relation thereto and defining said manually engageable portion, said elongate member including end portions extending from said central portion and along said arms outward to said couplers.

10. A fluid treating medical system comprising a heat exchanger and a holder for mounting said heat exchanger and supplying heat exchanging fluid to said heat exchanger, said heat exchanger including a pair of laterally spaced inlet and outlet fittings, said holder including a body having a pair of laterally spaced arms having inner ends interconnected by a transverse member, and free outer ends, two quick disconnect couplers, one mounted on the free outer end of each arm, releasably engaged with said inlet and outlet fittings, a release member having opposed ends fixed to said couplers for simultaneous disconnect manipulation thereof, said release member extending inwardly from said couplers along the corresponding arms and including a transverse portion intermediate said opposed ends and laterally spaced from said transverse member of said body for manual manipulation of said release member by an inward drawing of said transverse portion of said release member toward said body transverse member to effect a simultaneous disconnect of both couplers, said holder including means for communicating said couplers with supply and discharge lines for heat exchanging fluid.

11. The system of claim 10 including valve means for precluding flow through said couplers upon disconnect of said couplers from said heat exchanger fittings.

* * * * *